(12) United States Patent
Ma et al.

(10) Patent No.: US 11,045,068 B2
(45) Date of Patent: Jun. 29, 2021

(54) ENDOSCOPE LOCKING METHOD

(71) Applicant: SHENZHEN YATEKS OPTICAL ELECTRONIC TECHNOLOGY CO., LTD, Shenzhen (CN)

(72) Inventors: Tianyue Ma, Shenzhen (CN); Jiangfan Yan, Shenzhen (CN); Shaoming Lin, Shenzhen (CN)

(73) Assignee: SHENZHEN YATEKS OPTICAL ELECTRONIC TECHNOLOGY CO., LTD, Shenzhen (CN)

( * ) Notice: Subject to any disclaimer, the term of this patent is extended or adjusted under 35 U.S.C. 154(b) by 357 days.

(21) Appl. No.: 16/128,510

(22) Filed: Sep. 12, 2018

(65) Prior Publication Data
US 2019/0008359 A1 Jan. 10, 2019

Related U.S. Application Data

(63) Continuation of application No. PCT/CN2016/077353, filed on Mar. 25, 2016.

(51) Int. Cl.
*A61B 1/00* (2006.01)
*G02B 23/24* (2006.01)
*A61B 1/005* (2006.01)

(52) U.S. Cl.
CPC ...... *A61B 1/00006* (2013.01); *A61B 1/00039* (2013.01); *A61B 1/0052* (2013.01); *A61B 1/0055* (2013.01); *A61B 1/00078* (2013.01); *G02B 23/24* (2013.01); *A61B 1/0057* (2013.01)

(58) Field of Classification Search
CPC ............ A61B 1/00006; A61B 1/00039; A61B 1/00078; A61B 1/0052; A61B 1/0055; A61B 1/0057; G05G 9/04; G05G 9/047; G06F 3/0213; G06F 3/033; G06F 3/0338; G06F 3/038
USPC ..................... 345/161; 600/146, 118; 463/38
See application file for complete search history.

(56) References Cited

U.S. PATENT DOCUMENTS

| | | | | |
|---|---|---|---|---|
| 5,114,402 | A * | 5/1992 | McCoy | A61B 1/0051 600/143 |
| 5,658,238 | A * | 8/1997 | Suzuki | A61B 1/00039 600/146 |
| 5,874,944 | A * | 2/1999 | Khoury | G06F 1/3259 345/161 |
| 8,523,765 | B2 | 9/2013 | Kawai | |
| 8,864,656 | B2 | 10/2014 | Konstorum | |
| 2004/0267093 | A1 | 12/2004 | Miyagi et al. | |

(Continued)

OTHER PUBLICATIONS

Internation Search Report of PCT/CN2016/077353, dated Jan. 3, 2017.

*Primary Examiner* — Timothy J Neal
*Assistant Examiner* — Sung Ham
(74) *Attorney, Agent, or Firm* — IPro, PLLC (57) ABSTRACT

The disclosure provides an endoscope locking method in which a locking condition is set based on change in coordinates of a manipulation portion. When a sampled X coordinate and Y coordinate of the manipulation portion meet a set change in coordinates of the manipulation portion, a locking signal is sent out, and thus an endoscope is locked. The method can achieve one-hand manipulation, and automatically achieves the locking of the endoscope according to the change in coordinates of the manipulation portion.

18 Claims, 4 Drawing Sheets

(56) References Cited

U.S. PATENT DOCUMENTS

| | | | |
|---|---|---|---|
| 2008/0221592 A1* | 9/2008 | Kawai | A61B 1/0055 |
| | | | 606/130 |
| 2009/0018390 A1 | 1/2009 | Honda et al. | |
| 2010/0160728 A1 | 6/2010 | Yoshie | |
| 2011/0275896 A1 | 11/2011 | Tanaka | |
| 2015/0351610 A1* | 12/2015 | Fan | A61B 1/0057 |
| | | | 600/148 |
| 2018/0132699 A1* | 5/2018 | Inoue | A61B 1/00039 |

* cited by examiner

ENDOSCOPE LOCKING METHOD

CROSS-REFERENCE TO RELATED APPLICATIONS

This application is a continuation of International Patent Application No. PCT/CN2016/077353 with a filing date of Mar. 25, 2016, designating the United States, now pending. The content of the aforementioned application, including any intervening amendments thereto, is incorporated herein by reference.

TECHNICAL FIELD

The disclosure relates to an endoscope, and particularly to an endoscope locking method.

BACKGROUND OF THE PRESENT INVENTION

Angle control of endoscopes on the market is divided into a manual control manner and an electric control manner. In order to facilitate a careful viewing of situations of a monitoring body position in a certain direction, locking is often needed so as to perform fixed-point viewing.

The manual control manner is that a joystick is controlled by fingers to pull a steel wire so that a front end is bent for observation, such endoscope angle locking depends on a force of a finger and damp of a motion mechanism, and is achieved in a mechanical manner of clamping a steel wire by wrenching a bayonet, with great damage on the steel wire and affection on the service life of the steel wire. In the aspect of the locking angle, the traditional mechanical endoscope can only be locked in four directions without achieving locking of any angles, cannot achieve one-hand operation and is relatively strenuous when locking, and thus when the traditional mechanical endoscope is in high-strength use, a user has strong uncomfortable sense.

The electric control manner is that a steel wire is pulled through a power motion component such as a motor so that a front end is bent for observation. However, in order to lock at a certain angle for observation, the other hand is needed to perform key operation to trigger a locking signal, which belongs to semi-automatic control. Since the other hand of a user needs to grasp the outer end casing of the endoscope for observation, the practicability of the electrically controlled endoscope is greatly reduced.

SUMMARY OF PRESENT INVENTION

An endoscope locking method is provided according to one aspect of the disclosure.

The endoscope locking method includes:

A sampling step of acquiring an electric signal indicating coordinate information of a manipulation portion and converting the electric signal into an X coordinate and a Y coordinate of the manipulation portion, and sampling according to a set sampling frequency;

A locking determination step of setting a locking condition based on change in coordinates of the manipulation portion, and sending out a locking signal when the sampled X coordinate and Y coordinate of the manipulation portion meet a set change in coordinates of the manipulation portion; and A locking step of locking an endoscope.

As a further improvement of the endoscope locking method, the locking determination step includes a fixed-point locking mode of recording a sampled X coordinate and Y coordinate each time, comparing a next sampled X coordinate and Y coordinate with the last sampled X coordinate and Y coordinate after next sampling, and sending out the locking signal if the two X coordinates and Y coordinates are substantially equal.

As a further improvement of the endoscope locking method, in the fixed-point locking mode, timing is started when it is determined that previous and subsequent X coordinates and Y coordinates are substantially equal, and the locking signal is sent out when timing reaches or exceeds a set value.

As a further improvement of the endoscope locking method, the locking determination step includes a following locking mode of recording a sampled X coordinate and Y coordinate each time; when a next sampled X coordinate and Y coordinate are reset, using the previously sampled X coordinate and Y coordinate when in reset as an origin of coordinates, and sending out the locking signal to lock the endoscope in the origin of coordinates.

As a further improvement of the endoscope locking method, after the endoscope is locked, a new X coordinate and Y coordinate are accumulated on the basis of the origin of coordinates to obtain locking coordinates when the X coordinate and the Y coordinate of the manipulation portion change again; subsequently, each change is accumulated on the basis of previously obtained locking coordinates until unlocking, and a maximum coordinate value is used as an output value when an accumulation value exceeds a maximum coordinate limitation value.

The method is capable of switching between the following locking mode and the fixed-point locking mode; when the fixed-point locking mode is switched to the following locking mode, locking coordinates under the fixed-point locking mode are changed into the origin of coordinates under the following locking mode; and when the following locking mode is switched into the fixed-point locking mode, locking coordinates under the following locking mode are changed into the locking coordinates under the fixed-point locking mode.

According to the endoscope locking method of the disclosure, since a locking condition is set based on change in coordinates of the manipulation portion, the locking signal is sent out when a sampled X coordinate and Y coordinate meet change in set coordinates of the manipulation portion. Thus, one-hand manipulation can be achieved, and the endoscope is automatically locked according to change in coordinates of the manipulation portion.

DETAILED DESCRIPTION OF PREFERRED EMBODIMENTS

Embodiment 1

This embodiment 1 discloses an endoscope locking method, including:

A sampling step of acquiring an electric signal indicating coordinate information of a manipulation portion and converting the electric signal into an X coordinate and a Y coordinate of the manipulation portion, and sampling according to a set sampling frequency;

A locking determination step of setting a locking condition based on change in coordinates of a manipulation portion, and sending out a locking signal when a sampled X coordinate and Y coordinate of the manipulation portion meet a set change in coordinates of the manipulation portion; and A locking step of locking an endoscope.

Figure 1:
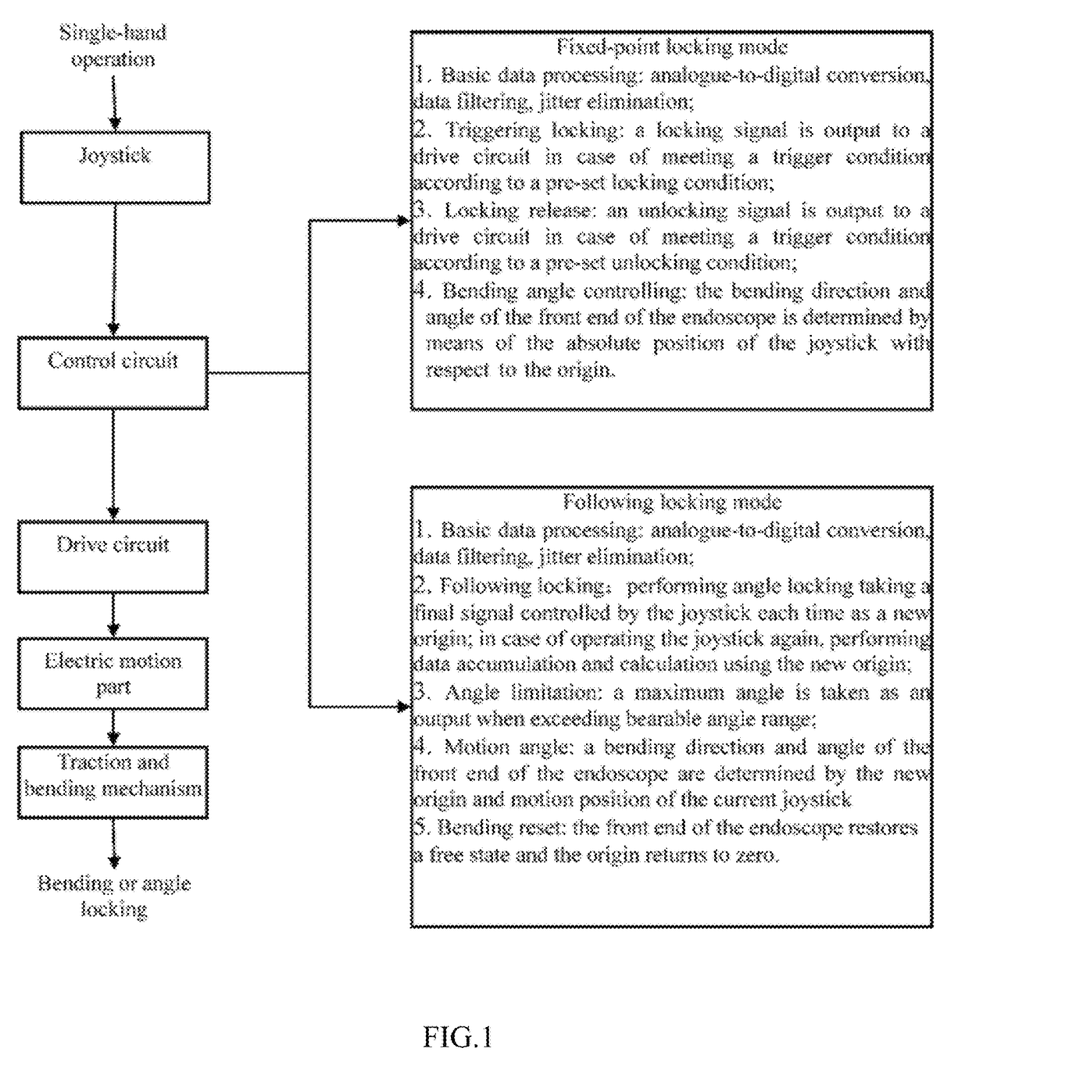
FIG. 1 is a structural topological diagram of a locking device for an endoscope locking method.
Figure 3:
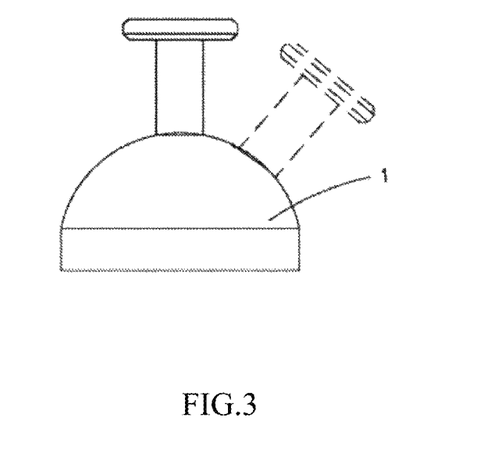
FIG. 3 is a schematic diagram of a joystick for the endoscope locking method.
Figure 4:
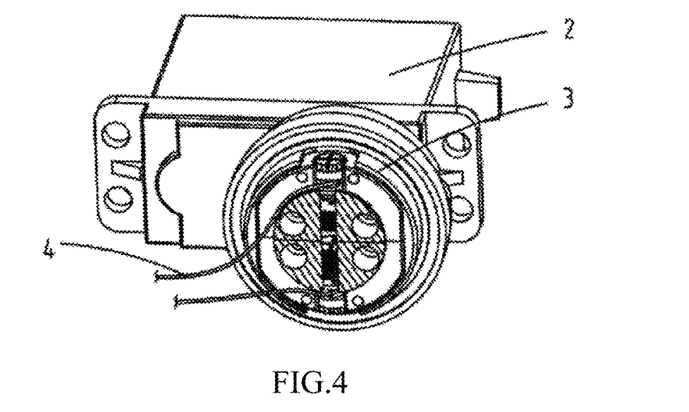
FIG. 4 is a schematic diagram of a power motion component for the endoscope locking method.
Figure 5:
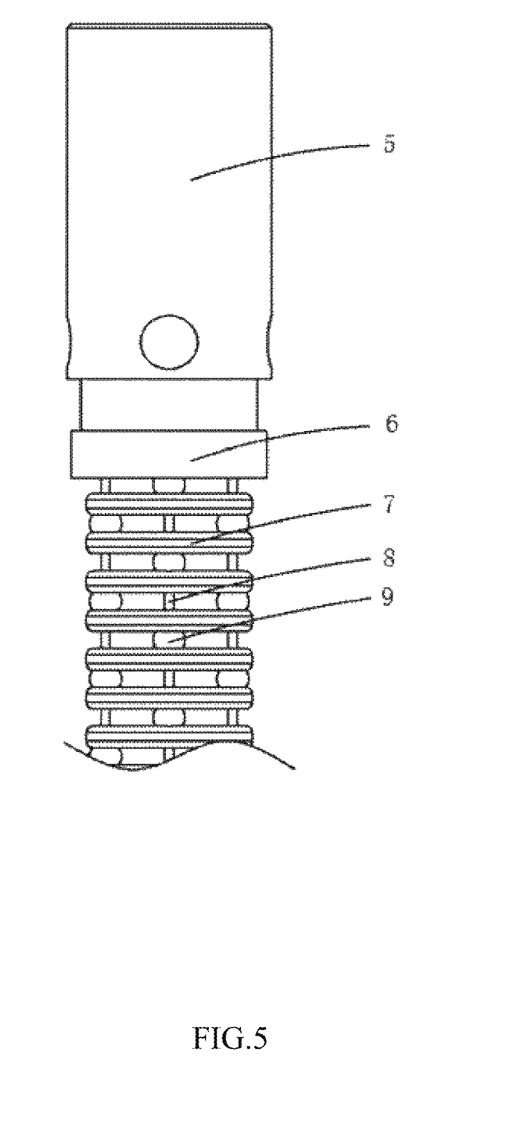
FIG. 5 is a schematic diagram of a traction and bending mechanism for the endoscope locking method.

The locking method will be illustrated with reference to an endoscope device for more clear illustration. FIG. 1 is a structural topological diagram of the locking device, and FIGS. 3-5 are schematic diagrams of a joystick, a power motion component and a traction and bending mechanism in this device. However, it is noted that this locking method is not limited to be achieved through the device shown in this embodiment 1.

Particularly, in the sampling step, the manipulation portion may be any device for allowing an operator to control the direction of the endoscope, for example, a joystick 1 as shown in FIG. 3.

The sampling step can be achieved in the following manner:

As shown in FIG. 1, the joystick 1 outputs two paths of analog signals, one path corresponds to an x axis, and the other path corresponds to a y axis.

Single chip microcomputer processing: a control circuit in this embodiment is realized in a single chip microcomputer. The x and y axis signals are converted into digital signals using analog-digital conversion, and then input into the single chip microcomputer to undergo data filtration and jitter elimination processing so as to obtain an x coordinate stabilizing value adx and a y coordinate stabilizing value ady (for example 0~3300, 1650 is median) corresponding to x and y axes.

Sampling is always performed with a set sampling frequency utilizing an AD converter, and a time interval between one sampling and next sampling is a reciprocal of the sampling frequency. The sampling frequency can be flexibly selected according to actual demand.

The locking determination step mainly determines in which cases a locking signal is sent out, so as to lock the endoscope.

Based on a concept that a locking condition is set based on change in coordinates of the manipulation portion, this embodiment discloses two modes of locking determination methods. Of course, the two locking determination methods can be simultaneously present, or locking is achieved adopting any one locking determination method. Meanwhile, other changes in coordinates of the manipulation portion are also used as a determination standard for giving the locking condition.

The two locking determination methods are respectively a fixed-point mode and a following locking mode, and are respectively described as follows.

The locking determination step includes the fixed-point locking mode of recording a sampled X coordinate and Y coordinate each time, comparing a next sampled X coordinate and Y coordinate with the last sampled X coordinate and Y coordinate after next sampling, and sending out the locking signal if the two X coordinates and Y coordinates are substantially equal.

Figure 2:
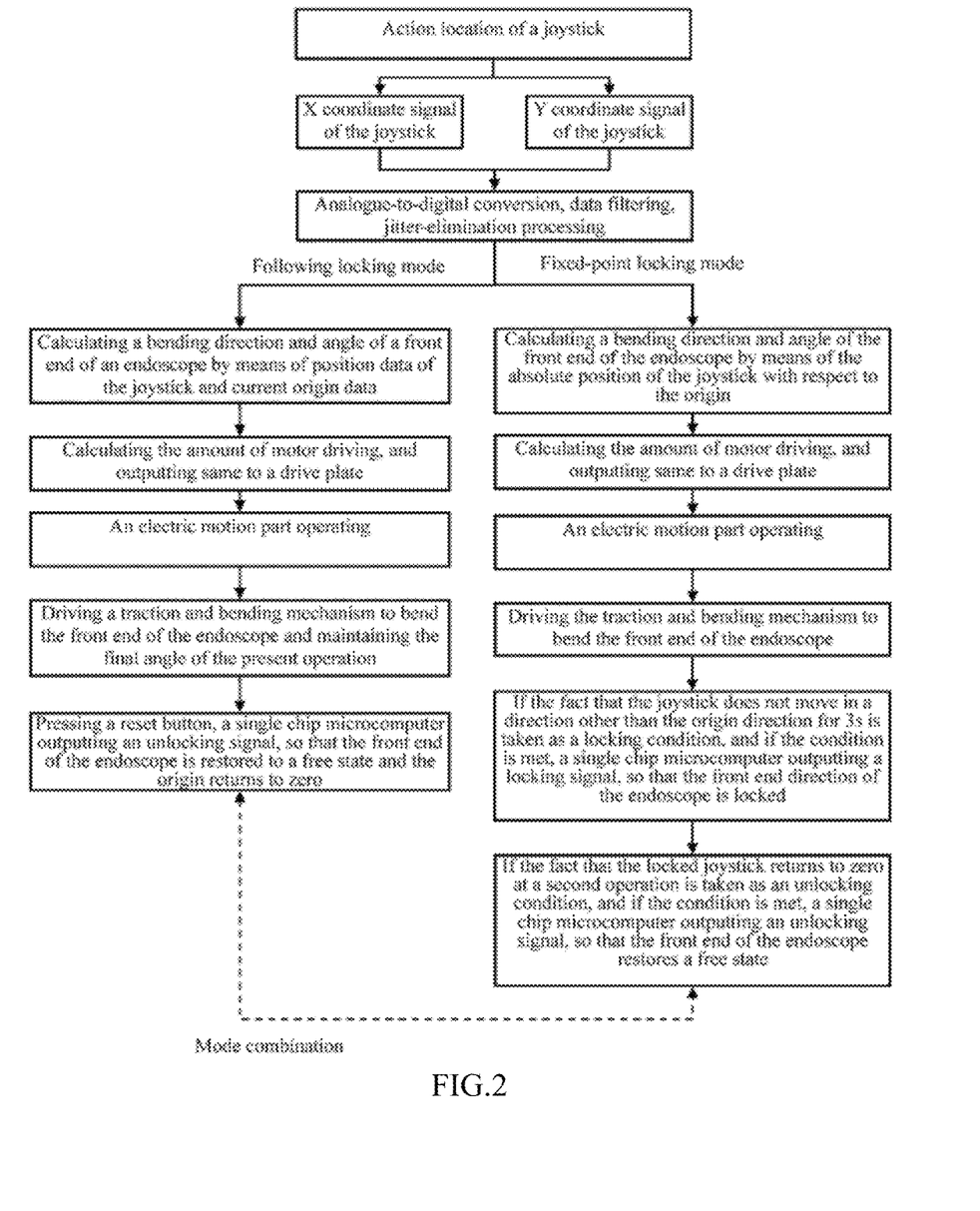
FIG. 2 is a data processing flowchart of the endoscope locking method.

Particularly, referring to FIGS. 1 and 2, in the fixed-point locking mode:

As shown in FIG. 3, the joystick 1 can move at any angle within a certain range. When the joystick 1 is shaken, adx and ady values correspondingly change; and when the joystick 1 stops, adx and ady are kept unchanged. Adx and ady values obtained by each sampling are stored. When next sampling is performed, the sampling values are compared with the previously stored values, and the locking signal is sent out to enter into a locking state if the previous and subsequent values are substantially equal. When the joystick 1 is loosened, the joystick 1 is automatically restored to an original position. However, the front end of the endoscope will be kept in a locking state.

The phrase "the joystick 1 stops" refers to a fact that a finger allows the joystick 1 to be static at a certain orientation. The term "substantially equal" described here permits fluctuation in a certain range, such as ±1% of fluctuation, beside including "equal" in a strict sense.

Further, after it is determined that the previous and subsequent values are substantially equal, the locking signal can be directly sent out, and a certain waiting time can also be set.

For instance, in the fixed-point locking mode, when it is determined that the previous and subsequent X coordinates and Y coordinates are substantially equal, timing is started; and when timing reaches or exceeds a set value such as 3000 ms, the locking signal is sent out.

In addition, when the previous and subsequent X coordinates and Y coordinates are substantially unequal, a timer is reset.

When unlocking is desired, unlocking can be performed in multiple forms several of which are only exemplarily described here:

1. An unlock button is specially set for unlocking. After the button is pressed, the single chip microcomputer outputs an unlocking signal, the front end of the endoscope is restored to be in a free state, and an origin is zeroed.

2. Unlocking is performed through action of the joystick 1, for example, after locking is completed, it is started to determine whether the locking state is released when the sampled X coordinate and Y coordinate are in a median, namely when the joystick 1 moves back to the median. In the process of determination, the unlocking signal is sent out if the sampled X coordinate and Y coordinate deviate from the median again.

Of course, based on consideration of mal-operation and user experience, mal-operation easily occurs if unlocking is caused by extremely small displacement; and user experience is bad if unlocking is caused by extremely large displacement. However, in the determination whether the locking state is released, the unlocking signal is sent out only when the sampled X coordinate or Y coordinate reaches or exceeds a set proportion (such as ⅓) of the maximum value thereof.

Here, the phase "reaches or exceeds ⅓ of the maximum value thereof" refers to a fact that when the joystick 1 is in a center, adx=ady=0; when the joystick 1 is in a maximum activation boundary in an x direction, a value in the x direction is maximum, and is Xa; when the joystick 1 is in a maximum activation boundary in a y direction, a value in the y direction is maximum, and is Ya. ⅓ position refers to a position where the joystick 1 moves ⅓ from the center to the maximum activation boundary, at this moment, the adx value or ady value is a value of ⅓ position, and this value is exceeded if acting toward the boundary.

3. After locking, the unlocking signal is sent out when temperatures of parts in the endoscope exceed a set temperature, for example, the temperature of the front end of the endoscope exceeds 80° C. or the temperature of a battery in the endoscope exceeds 70° C.

4. The unlocking signal is sent out when the pull force value of the traction and bending mechanism in the endoscope exceeds a set pull force value. For example, the pull force value of the traction and bending mechanism in the endoscope exceeds 100N.

Any one or more manners can be optionally selected for unlocking, and after unlocking, the front end of the endoscope is restored to an initially natural state.

The locking determination step includes a following locking mode of recording a sampled X coordinate and Y coordinate each time, and when a next sampled X coordinate and Y coordinate are reset, using the previously sampled X coordinate and Y coordinate as an origin of coordinates and sending out a locking signal to lock the endoscope in the origin of coordinates.

Particularly, referring to FIGS. 1 and 2, in the following locking mode:

When the joystick 1 is shaken, adx and ady values correspondingly change; when the joystick 1 is reset, data of adx and ady sampled when the joystick 1 is reset are kept, and the locking signal is output to lock the front end of the endoscope at the angle before the joystick 1 is reset.

Adx and ady values obtained before each resetting are stored. When the joystick 1 is shaken again next time, a sampled new value is added with the previously stored value as coordinates. A maximum coordinate range (for example 0~3300) is limited, and a maximum coordinate value is used as an output value when an accumulation value exceeds a maximum coordinate limitation value.

In order to achieve a following locking function, namely, achieve accumulation of coordinates and following and locking of angles, namely, locking is maintained after moving at each step, for example, the angle of the front end is controlled to (30°, 60°) for the first time, the coordinate of the joystick 1 is (15, 30), after a direction is locked, the front end is kept unchanged at 30°, and at this moment, the joystick 1 returns back to a central point so as not to cause the change of the angle of the front end. The joystick 1 is then shaken again, the coordinate of the joystick 1 is (−15, 30), and therefore the accumulated coordinate becomes (0, 60), the angle becomes (0°, 120°), and an angle locking state is maintained.

In such a mode, when unlocking is desired, similarly, unlocking is performed in multiple forms as well, such as first, third and fourth unlocking manners as described above, etc.

The above fixed-point locking mode and following locking mode can be applied alone, or can be simultaneously present in the same locking solution. When the fixed-point locking mode and the following locking mode are simultaneously present, they can be mutually switched.

Regardless of a free state or a locking state, they can be switched between the fixed-point locking mode and the following locking mode. After the fixed-point locking mode is used to lock the front end of the endoscope at a certain angle, the locking coordinate under the fixed-point locking mode becomes the origin coordinate under the following locking mode when the fixed-point mode is switched to the following locking mode; after the following locking mode is used to lock the front end of the endoscope at a certain angle, the locking coordinate of the following locking mode becomes the locking coordinate under the fixed-point locking mode when the following locking mode is switched to the fixed-point mode.

In the locking step, the endoscope is locked according to the locking signal.

Particularly, referring to FIGS. 1, 2, 4 and 5, the power motion component includes a steering engine 2, a wheel 3 and a steel wire 4. The steering engine 2 drives the wheel 3 to rotate, and the wheel 3 drives the steel wire 4, so as to deliver a force to a traction and bending mechanism.

The traction and bending mechanism includes a front end 5 of an endoscope, a snake bone lens connection member 6, a snake bone ring 7 and a snake bone bead 9. The steel wire 8 passes through the snake bone ring 7, the snake bone bead 9 and the snake bone lens connection member 6 to allow the direction of the front end 5 of the endoscope to be changed. Since the snake bone ring 7 and the snake bone bead 9 are moveable, the steel wire 8 is subjected to the pull force, and the snake bone ring 7 and the snake bone bead 9 are bent because a support point is subjected to the force. The snake bone ring 7 and the snake bone bead 9 drive the snake bone lens connection member 6 to be bent together with the front end 5 of the endoscope, thereby achieving a bending or angle locking function in any direction.

The x coordinate stabilizing value adx and the y coordinate stabilizing value ady of the joystick 1 are converted into an input signal of a drive board:

$$pwmx = \frac{(PWM\_MAX - PWM\_MIN) * adx + (AD\_MAX * PWM\_MIN - AD\_MIN * PWM\_MAX)}{AD\_MAX - AD\_MIN}$$

$$pwmy = \frac{(PWM\_MAX - PWM\_MIN) * ady + (AD\_MAX * PWM\_MIN - AD\_MIN * PWM\_MAX)}{AD\_MAX - AD\_MIN}$$

wherein, pwmx is an impulse width value of the steering engine at the x axis, pwmy is an impulse width value of the steering engine at the y axis, PWM_MAX is a maximum impulse width value of the steering engine, PWM_MIN is a minimum impulse width value of the steering engine, AD_MIN is a minimum ad value of the joystick 1, and AD_MAX is a maximum ad value of the joystick 1.

Then, the drive board receives an impulse width signal processed by the single chip microcomputer to drive the x-axis steering engine and the y-axis steering engine to move. In this embodiment, the motion angle of the steering engine is 0~330°.

The x-axis steering engine and the y-axis steering engine achieve functions of bending and locking the endoscope at a certain angle, resetting and the like under the drive of the drive board.

In this embodiment, a function of controlling the value of the bending angle of the front end of the endoscope is achieved through the distance between the joystick 1 and the origin by establishing a relationship among the position size of the joystick 1, the motion amount of the power motion component, the tension amount of the traction and bending mechanism and the bending angle of the front end of the endoscope.

In this embodiment, a function of locking the bending angle of the front end of the endoscope by one hand and a function of releasing angle locking by one hand are achieved through a manner of controlling the trigger of a circuit condition under the fixed-point locking mode.

A function of controlling the size of the bending angle of the front end of the endoscope is achieved through accumulating the electric signal of the joystick 1 with the origin of coordinates by establishing a relationship among the position size of the joystick 1, the updating and iteration of the origin of the joystick 1 and the bending angle of the front end of the endoscope under the following locking mode. A function of following and locking the bending angle of the front end of the endoscope by one hand is achieved in a manner of automatically locking a new origin.

The above two methods and a mutual combination form thereof solve practical problems of discomfort of the endoscope when in high-strength use adopting a manual control manner, locking at any angle, locking service life of the steel wire, one-hand operation and the like.

The disclosure is described with reference to particular examples as set forth above, and these examples are only for better understanding of the invention instead of limiting the invention. One of ordinary skill in the art can make variations or modifications to above embodiments under the teaching of this disclosure.

We claim:

1. An endoscope locking method, comprising:
   a sampling step of acquiring an electric signal indicating coordinate information of a manipulation portion and converting the electric signal into an X coordinate and a Y coordinate of the manipulation portion, and sampling according to a set sampling frequency;
   a locking determination step of setting a locking condition based on change in coordinates of the manipulation portion, and sending out a locking signal when a sampled X coordinate and Y coordinate of the manipulation portion meet a set change in coordinates of the manipulation portion; and
   a locking step of locking an endoscope according to the locking signal;
   an unlocking step of unlocking the locked endoscope and restoring a front end of the endoscope to an initially natural state;
   wherein, the locking determination step comprises a following locking mode of
   recording a sampled X coordinate and Y coordinate each time; and when the manipulation portion is reset, using the previously sampled X coordinate and Y coordinate as an origin of coordinates, and sending out the locking signal to lock the endoscope in the origin of coordinates such that the front end of the endoscope is locked at an angle before the manipulation portion is reset.

2. The endoscope locking method according to claim 1, wherein, the locking determination step comprises a fixed-point locking mode of recording the sampled X coordinate and Y coordinate each time, comparing a next sampled X coordinate and Y coordinate with the last sampled X coordinate and Y coordinate after next sampling, and sending out the locking signal if the two X coordinates and Y coordinates are substantially equal.

3. The endoscope locking method according to claim 2, wherein, in the fixed-point locking mode, timing is started when it is determined that previous and subsequent X coordinates and Y coordinates are substantially equal, and the locking signal is sent out when timing reaches or exceeds a set value.

4. The endoscope locking method according to claim 3, wherein, a timer is reset when it is determined that previous and subsequent X coordinates and Y coordinates are unequal.

5. The endoscope locking method according to claim 2, wherein, the locking determination step further comprises a following locking mode of recording a sampled X coordinate and Y coordinate each time; when the manipulation portion is reset, using previously sampled X coordinate and Y coordinate as an origin of coordinates, and sending out a locking signal to lock the endoscope in the origin of coordinates such that a front end of the endoscope is locked at an angle before the manipulation portion is reset; after the endoscope is locked, accumulating a new X coordinate and Y coordinate on the basis of the origin of coordinates to obtain locking coordinates when the X coordinate and the Y coordinate of the manipulation portion change again; and accumulating subsequent each change on the basis of previously obtained locking coordinates until unlocking, and a maximum coordinate value is used as an output value when an accumulation value exceeds a maximum coordinate limitation value;
   the method is capable of switching between the following locking mode and the fixed-point locking mode; when the fixed-point locking mode is switched to the following locking mode, locking coordinates under the fixed-point locking mode are changed into the origin of coordinates under the following locking mode; and when the following locking mode is switched into the fixed-point locking mode, locking coordinates under the following locking mode are changed into the locking coordinates under the fixed-point locking mode.

6. The endoscope locking method according to claim 1, wherein the unlocking step comprises
   starting determining whether a locking state is released when the sampled X coordinate and Y coordinate are in a median after locking is completed, wherein in the process of determination, an unlocking signal is sent out if the sampled X coordinate or Y coordinate deviates from the median again.

7. The endoscope locking method according to claim 6, wherein, in the determination that whether the locking state is released, the unlocking signal is sent out when the sampled X coordinate or Y coordinate reaches or exceeds a set proportion of a maximum value thereof.

8. The endoscope locking method according to claim 1, wherein, after the endoscope is locked, a new X coordinate and Y coordinate are accumulated on the basis of the origin of coordinates to obtain locking coordinates when the X coordinate and the Y coordinate of the manipulation portion change again; subsequently, each change is accumulated on the basis of previously obtained locking coordinates until unlocking, and a maximum coordinate value is used as an output value when an accumulation value exceeds a maximum coordinate limitation value.

9. The endoscope locking method according to claim 1, wherein the unlocking step comprises:
   sending out an unlocking signal when temperatures of parts in the endoscope exceed a set temperature after locking; or
   sending out the unlocking signal when a tensile force value of a traction mechanism in the endoscope exceeds a set tensile force value.

10. An endoscope locking method, comprising:
    a sampling step of acquiring an electric signal indicating coordinate information of a manipulation portion and converting the electric signal into an X coordinate and a Y coordinate of the manipulation portion, and sampling according to a set sampling frequency;
    a locking determination step of setting a locking condition based on change in coordinates of the manipulation portion, and sending out a locking signal when a sampled X coordinate and Y coordinate of the manipulation portion meet a set change in coordinates of the manipulation portion; and a locking step of locking an endoscope according to the locking signal;

wherein, the locking determination step comprises a following locking mode of recording a sampled X coordinate and Y coordinate each time; and when the manipulation portion is reset, using the previously sampled X coordinate and Y coordinate as an origin of coordinates, and sending out the locking signal to lock the endoscope in the origin of coordinates such that a front end of the endoscope is locked at an angle before the manipulation portion is reset.

11. The endoscope locking method according to claim 10, wherein, after the endoscope is locked, a new X coordinate and Y coordinate are accumulated on the basis of the origin of coordinates to obtain locking coordinates when the X coordinate and the Y coordinate of the manipulation portion change again; subsequently, each change is accumulated on the basis of previously obtained locking coordinates until unlocking, and a maximum coordinate value is used as an output value when an accumulation value exceeds a maximum coordinate limitation value.

12. The endoscope locking method according to claim 10, wherein, the locking determination step comprises a fixed-point locking mode of recording the sampled X coordinate and Y coordinate each time, comparing a next sampled X coordinate and Y coordinate with the last sampled X coordinate and Y coordinate after next sampling, and sending out the locking signal if the two X coordinates and Y coordinates are substantially equal.

13. The endoscope locking method according to claim 12, wherein, the method is capable of switching between the following locking mode and the fixed-point locking mode; when the fixed-point locking mode is switched to the following locking mode, locking coordinates under the fixed-point locking mode are changed into the origin of coordinates under the following locking mode; and when the following locking mode is switched into the fixed-point locking mode, locking coordinates under the following locking mode are changed into the locking coordinates under the fixed-point locking mode.

14. The endoscope locking method according to claim 12, further comprising an unlocking step of sending out an unlocking signal when temperatures of parts in the endoscope exceed a set temperature after locking; or sending out the unlocking signal when a tensile force value of a traction mechanism in the endoscope exceeds a set tensile force value.

15. The endoscope locking method according to claim 12, wherein, in the fixed-point locking mode, timing is started when it is determined that previous and subsequent X coordinates and Y coordinates are substantially equal, and the locking signal is sent out when timing reaches or exceeds a set value.

16. The endoscope locking method according to claim 15, wherein, a timer is reset when it is determined that previous and subsequent X coordinates and Y coordinates are unequal.

17. The endoscope locking method according to claim 12, wherein the unlocking step comprises:

starting determining whether a locking state is released when the sampled X coordinate and Y coordinate are in a median after locking is completed, wherein in the process of determination, an unlocking signal is sent out if the sampled X coordinate or Y coordinate deviates from the median again.

18. The endoscope locking method according to claim 17, wherein, in the determination that whether the locking state is released, the unlocking signal is sent out when the sampled X coordinate or Y coordinate reaches or exceeds a set proportion of a maximum value thereof.

* * * * *